United States Patent
Feldman et al.

(10) Patent No.: US 10,352,776 B2
(45) Date of Patent: *Jul. 16, 2019

(54) TEMPERATURE SENSING CIRCUITRY FOR AN IMPLANTABLE MEDICAL DEVICE

(71) Applicant: Boston Scientific Neuromodulation Corporation, Valencia, CA (US)

(72) Inventors: Emanuel Feldman, Simi Valley, CA (US); Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/926,418

(22) Filed: Mar. 20, 2018

(65) Prior Publication Data

US 2018/0209854 A1 Jul. 26, 2018

Related U.S. Application Data

(63) Continuation of application No. 14/599,745, filed on Jan. 19, 2015, now Pat. No. 9,958,339.

(Continued)

(51) Int. Cl.
*B41J 2/35* (2006.01)
*G01K 7/16* (2006.01)
(Continued)

(52) U.S. Cl.
CPC ........... *G01K 7/16* (2013.01); *A61N 1/36125* (2013.01); *A61N 1/3706* (2013.01); *G01K 7/015* (2013.01);
(Continued)

(58) Field of Classification Search
CPC .. G01K 7/16; G01K 7/22; G01K 7/20; G01K 7/183; G01K 13/002; G01K 7/015;
(Continued)

(56) References Cited

U.S. PATENT DOCUMENTS 5,122,637 A * 6/1992 Bottorff ................. B23K 3/033
219/229
5,225,811 A * 7/1993 Audy ................... G08B 21/182
307/117

(Continued)

*Primary Examiner* — Harshad R Patel
*Assistant Examiner* — Nigel H Plumb
(74) *Attorney, Agent, or Firm* — Lewis & Reese, PLLC

(57) ABSTRACT

Temperature sensing circuitry for an Implantable Medical Device (IMD) is disclosed that can be integrated into integrated circuitry in the IMD and draws very little power, thus enabling continuous temperature monitoring without undue battery depletion. Temperature sensor and threshold setting circuitry produces analog voltage signals indicative of a sensed temperature and at least one temperature threshold. Such circuitry employs a Ptat current reference stage and additional stages, which stages contains resistances that are set based on the desired temperature threshold(s) and to set the voltage range of the sensed temperature. These analog voltages are received at temperature threshold detection circuitry, which produces digital signal(s) indicating whether the sensed temperature has passed the temperature threshold(s). The digital signal(s) are then provided to digital circuitry in the IMD, where they can be stored as a function of time for later review, or used to immediately to control IMD operation.

20 Claims, 14 Drawing Sheets

Related U.S. Application Data

(60) Provisional application No. 61/937,309, filed on Feb. 7, 2014.

(51) Int. Cl.
*A61N 1/36* (2006.01)
*A61N 1/37* (2006.01)
*G01K 7/01* (2006.01)
*G01K 13/00* (2006.01)
*H01M 10/48* (2006.01)
*A61N 1/372* (2006.01)

(52) U.S. Cl.
CPC .. *G01K 13/002* (2013.01); *A61N 2001/37294* (2013.01); *H01M 10/486* (2013.01)

(58) Field of Classification Search
CPC ...... G01K 7/01; G01N 17/00; A61N 1/36125; A61N 1/3706; A61N 2001/37294; H01M 10/486
See application file for complete search history.

(56) References Cited

U.S. PATENT DOCUMENTS

| | | | |
|---|---|---|---|
| 6,516,227 B1 | 2/2003 | Meadows et al. | |
| 6,567,763 B1 * | 5/2003 | Javanifard | G01K 7/01 374/173 |
| 7,426,413 B2 * | 9/2008 | Balczewski | A61B 5/0008 374/E13.002 |
| 7,809,519 B2 * | 10/2010 | Sinha | G01K 7/015 702/99 |
| 9,958,339 B2 * | 5/2018 | Feldman | G01K 7/16 |
| 2007/0014329 A1 | 1/2007 | Sinha | |
| 2011/0001546 A1 * | 1/2011 | Guo | G01K 3/005 327/512 |
| 2011/0087307 A1 * | 4/2011 | Carbunaru | A61N 1/3605 607/61 |
| 2012/0095529 A1 * | 4/2012 | Parramon | A61N 1/025 607/59 |
| 2013/0057995 A1 * | 3/2013 | Feldtkeller | G01K 7/01 361/87 |
| 2013/0121377 A1 * | 5/2013 | Furuichi | G01K 7/01 374/178 |
| 2015/0080982 A1 * | 3/2015 | Van Funderburk | A61N 1/37217 607/59 |

\* cited by examiner

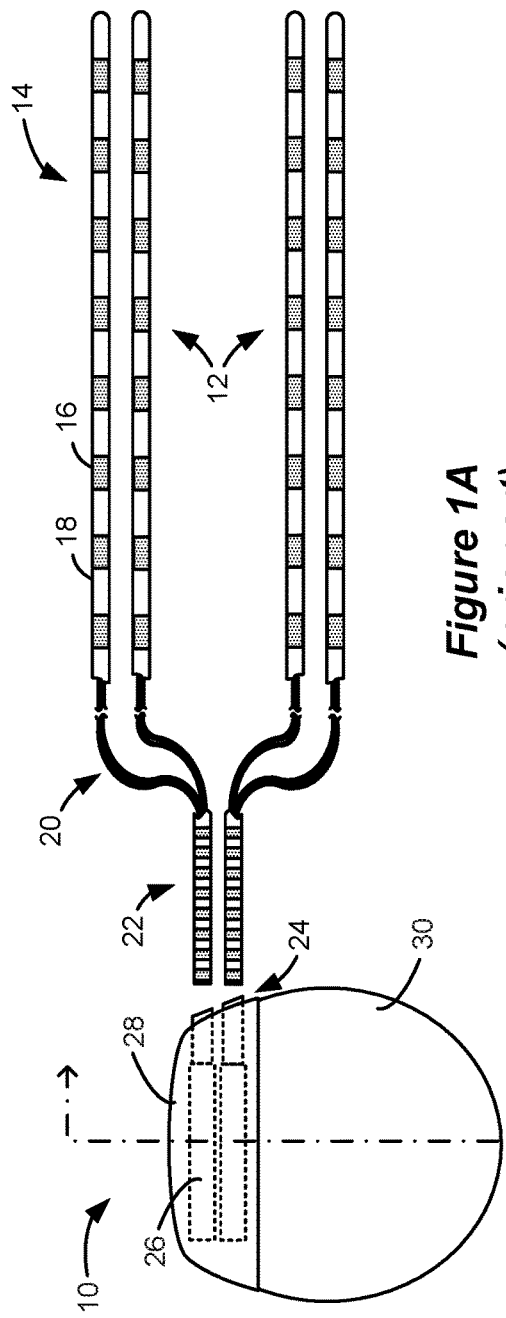
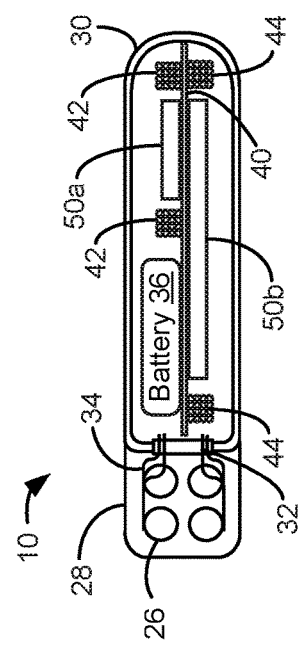
*Figure 1A (prior art)*
*Figure 1B (prior art)*

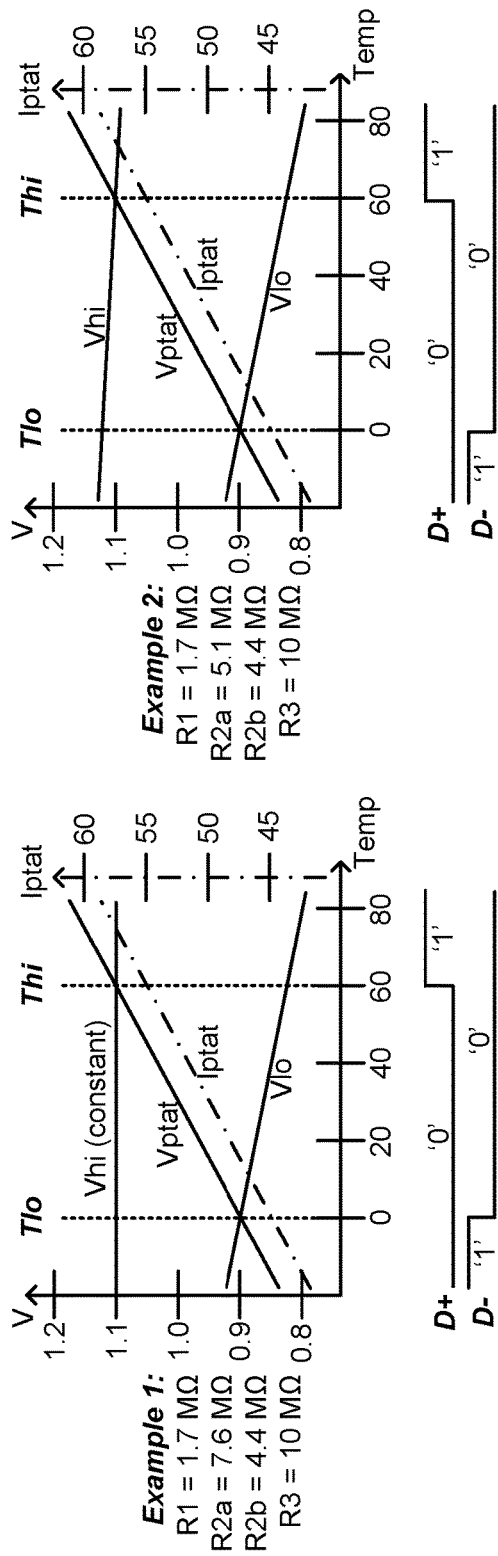
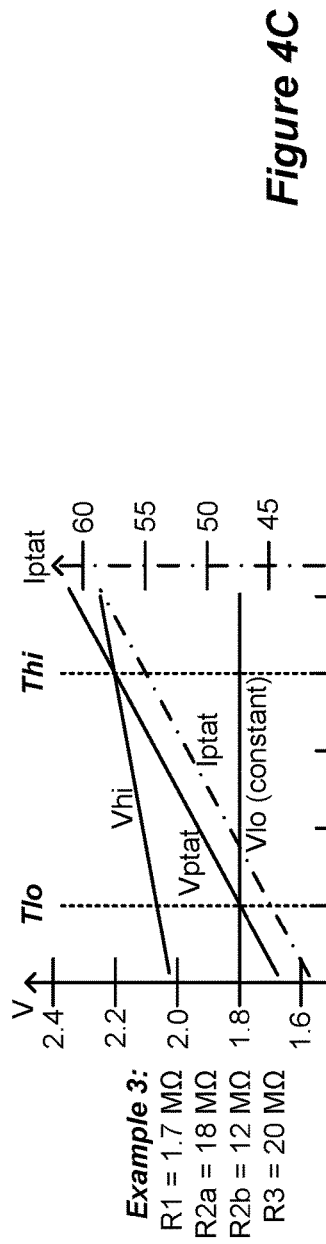
*Figure 4C*

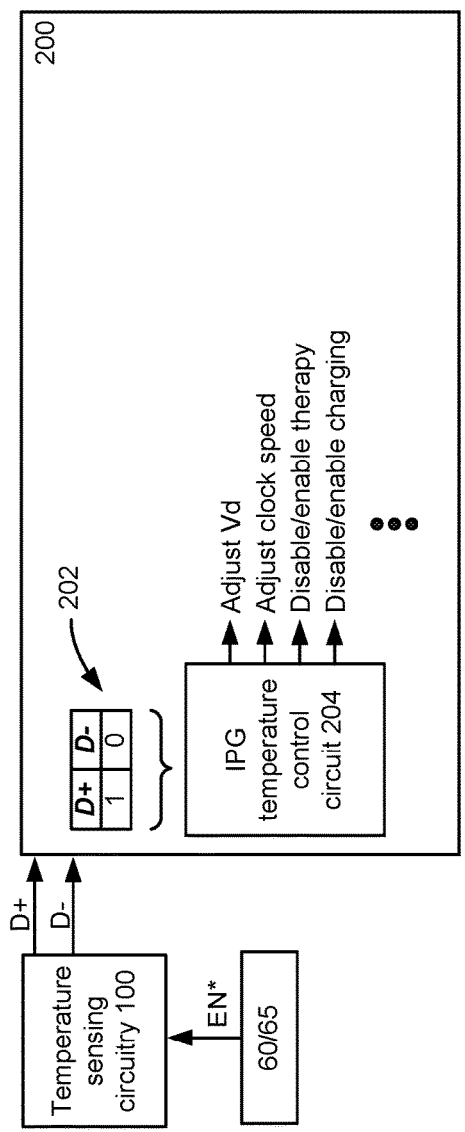
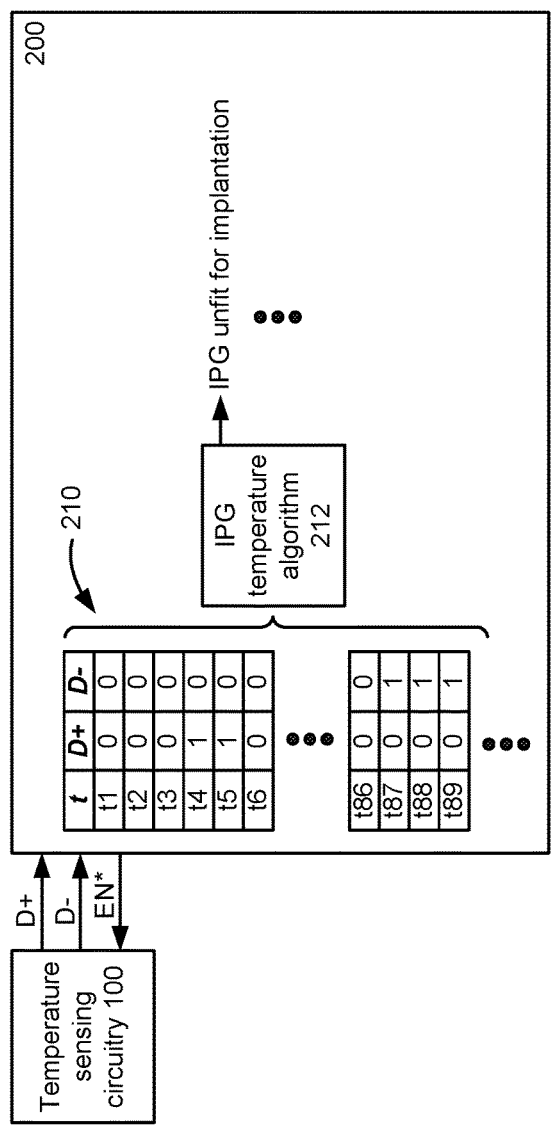

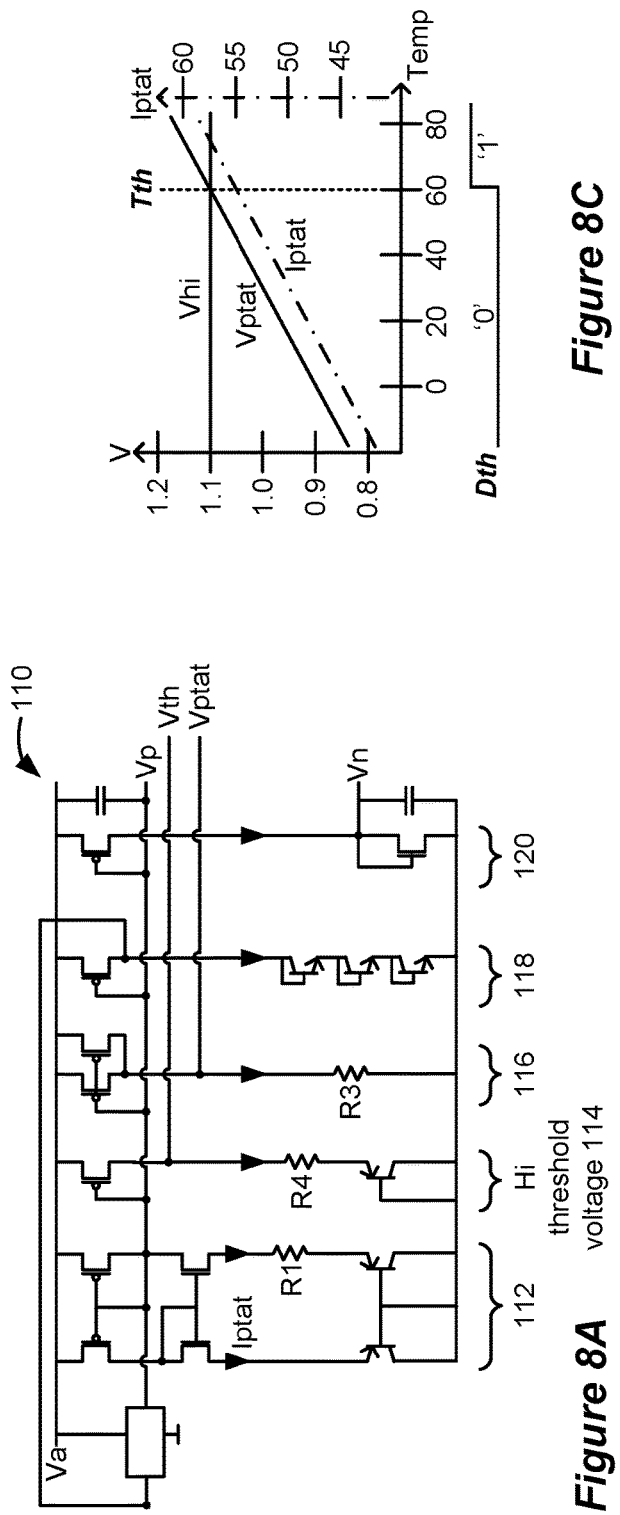
*Figure 8C*
*Figure 8A*
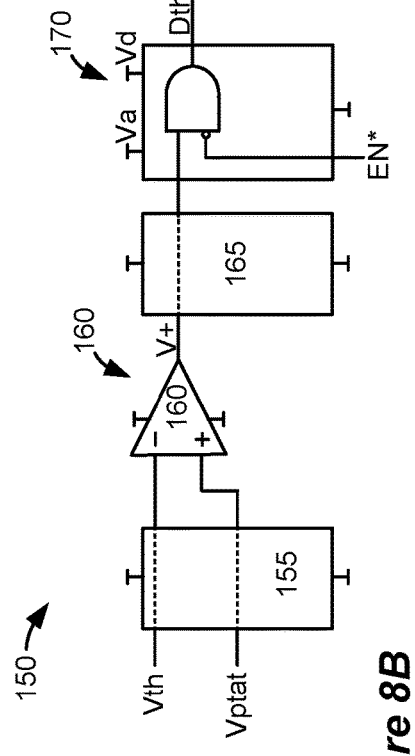
*Figure 8B*

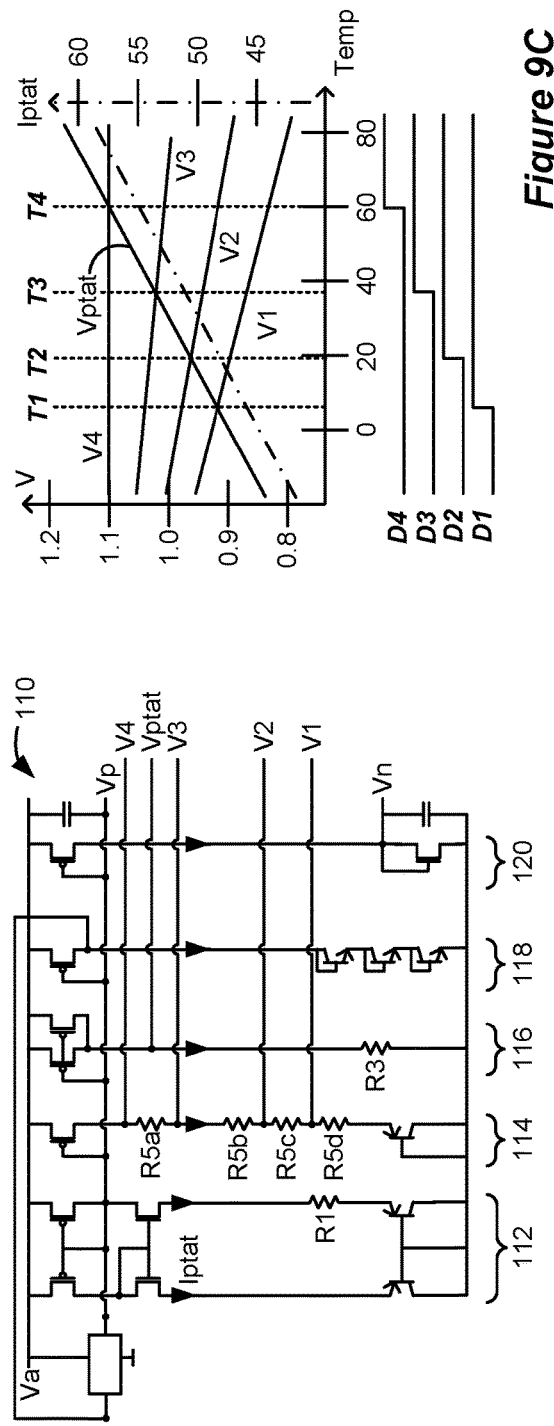
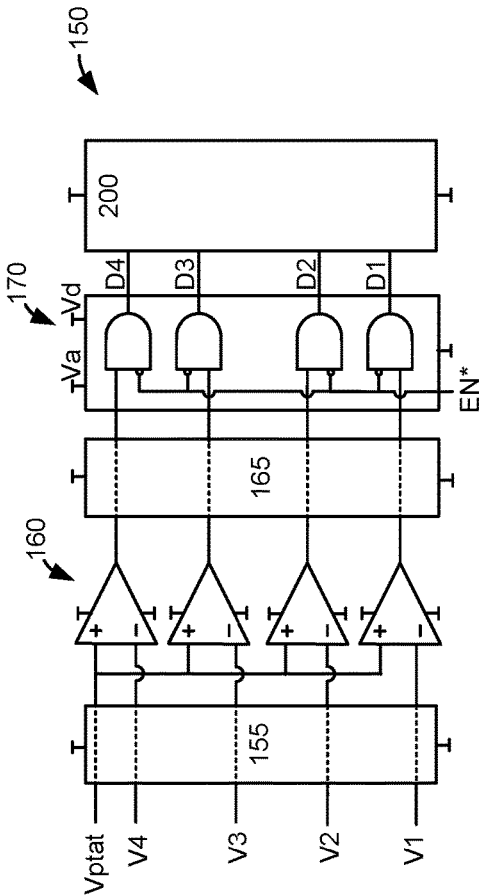
*Figure 9C*
*Figure 9A*
*Figure 9B*

TEMPERATURE SENSING CIRCUITRY FOR AN IMPLANTABLE MEDICAL DEVICE

CROSS REFERENCE TO RELATED APPLICATIONS

This application is a continuation of U.S. Non-Provisional patent application Ser. No. 14/599,745, filed Jan. 19, 2015, which is a non-provisional of U.S. Provisional Patent Application Ser. No. 61/937,309, filed Feb. 7, 2014. Priority is claimed to these applications, and they are incorporated herein by reference in their entireties.

FIELD OF THE INVENTION

This application relates to the field of implantable medical devices, and in particular to temperature sensor circuitry for implantable medical devices, or for other devices and integrated circuits.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device, or in other non-medical devices as well.

An SCS system typically includes an Implantable Pulse Generator (IPG) 10 shown in plan and cross-sectional views in FIGS. 1A and 1B. The IPG 10 includes a biocompatible device case 30 that holds the circuitry and battery 36 necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26, which are in turn coupled by feedthrough pins 34 through a case feedthrough 32 to circuitry within the case 30.

In the illustrated IPG 10, there are thirty-two lead electrodes (E1-E32) split between four leads 14, with the header 28 containing a 2×2 array of lead connectors 24. However, the number of leads and electrodes in an IPG is application specific and therefore can vary. In a SCS application, the electrode leads 14 are typically implanted proximate to the dura in a patient's spinal cord, and when a four-lead IPG 10 is used, these leads are usually split with two on each of the right and left sides of the dura. The proximal electrodes 22 are tunneled through the patient's tissue to a distant location such as the buttocks where the IPG case 30 is implanted, at which point they are coupled to the lead connectors 24. A four-lead IPG 10 can also be used for Deep Brain Stimulation (DBS) in another example. In other IPG examples designed for implantation directly at a site requiring stimulation, the IPG can be lead-less, having electrodes 16 instead appearing on the body of the IPG for contacting the patient's tissue.

As shown in the cross section of FIG. 1B, the IPG 10 includes a printed circuit board (PCB) 40. Electrically coupled to the PCB 40 are the battery 36 (which may rechargeable or permanent); other circuitry 50a and 50b coupled to top and bottom surfaces of the PCB (discussed further below with respect to FIG. 2); a telemetry coil 42 for wirelessly communicating with an external controller (not shown); a charging coil 44 for wirelessly receiving a magnetic charging field from an external charger (not shown) for recharging the battery 36 (if it is rechargeable) or for receiving continuous external power; and the feedthrough pins 34 (connection not shown). Further details concerning operation of the coils 42 and 44 and the external devices with which they communicate can be found in U.S. Patent Application Publication 2015/0080982.

FIG. 2 shows the basic architecture of the circuitry within the IPG 10, and further details can be found in U.S. Patent Application Publication 2012/0095529, which is incorporated herein by reference. As shown, the IPG 10 includes a microcontroller 60 and one or more Application Specific Integrated Circuits (ASICs) 65 that communicate via a digital bus 75 and by off-bus signals. ASIC(s) 65 can include circuitry necessary for IPG 10 operation, including current generation circuitry (used to provide specified current pulses to selected ones of the electrodes 16); telemetry circuitry (for modulating and demodulating data associated with the telemetry coil 42); battery management circuitry (for controlling the connection of the battery 36 to the remaining circuitry, and/or to control its charging via charging coil 44); various measurement and generator circuits; system memory; etc. Off-chip components on the PCB 40 that would typically couple to the ASIC(s) 65 or the microcontroller 60, but which are not shown in FIG. 2 for convenience, include the battery 36; the charging coil 44; the telemetry coil 42; various DC-blocking capacitors coupled to the electrodes 16; and other components of lesser relevance here. Microcontroller 60 may comprise in one example Part Number MSP430, manufactured by Texas Instruments, which is described in data sheets at http://www.ti.com/lsds/ti/microcontroller/16-bit_msp430/overview.page? DCMP=MCU_other& HQS=msp430, which is incorporated herein by reference. The ASIC(s) 65 may be as described in the above-incorporated '529 Publication.

Also included off-chip is a thermistor 80, which can be used to detect the temperature of the IPG 10. The thermistor 80 is typically included in a resistive network, and in the simple example shown is coupled in series to a resistor R0, although other networks could be used with the thermistor. This series connection receives Va, which is a power supply voltage generated and regulated from the voltage provided by the battery 36 (such regulation not shown) and generally used to power analog circuitry in the IPG 10, which power supply Va may be a few Volts or so. As the resistance of thermistor 80 changes (e.g., decreases with increasing temperature), the voltage drop V0 across R0 changes (e.g., increases with increasing temperature), which voltage drop is reported to the microcontroller 60 at one of its Analog-to-Digital converter (A/D) inputs 61 to inform the microcontroller 60 of the IPG's temperature. Resistor R0 in the resistive network may also be adjustable or programmable, as discussed further below. Alternatively, the temperature as discerned from the thermistor 80's resistive network may be provided to the ASIC(s) 65, which may filter and buffer the analog signal, and provide it to the microcontroller 60 via an off-bus analog signal trace (not shown) for digitization.

It is useful to detect the temperature of the IPG 10 for many reasons. For example, once an IPG's manufacture is complete but before it is implanted in a patient, it may be necessary to verify that the IPG has not been subject to temperatures that are too hot or too cold. Exposure to extreme temperatures could occur for example when IPGs are being distributed to implanting clinicians. For example, if IPGs are shipped via airplane in a cargo hold that is not well temperature controlled, they may be exposed to temperatures that are too cold (e.g., <0 C). Or if shipped by truck for example, they may be exposed to temperatures that are too hot (e.g., >60 C). Monitoring for exposure to such extreme temperatures is important because such exposure can affect IPG quality and reliability. For example, the battery 36 included in the IPG 10, whether rechargeable or not, may become damaged at such extreme temperatures, even if such exposure is merely temporary. In fact, detecting of ambient temperatures during IPG distribution is a significant enough issue that temperature sensors external to the IPG can be included with their shipment, such as sensors placed on or in a box containing a number of IPGs being shipped. If IPGs are exposed to extreme temperatures, they may need to be returned to the manufacturer as unsuitable for implantation in a patient.

Another example in which detecting IPG 10 temperature is useful is during charging of the battery 36, assuming it is rechargeable, or otherwise when the IPG is receiving external power from an external charger. As is known, receipt of a magnetic charging field from an external charger can cause the IPG's temperature to increase, both by virtue of heating of the circuitry coupled to the charging coil 44 that receives and processes the received power, and by the induction of Eddy currents in conductive structures in the IPG 10, such as case 30. As explained in U.S. Patent Application Publication 2011/0087307, heating of the IPG 10 during charging can aggravate or damage a patient's tissue if a safe temperature is exceeded (e.g., >41 C). Thus, the microcontroller 60 can monitor whether thermistor 80 is reporting a temperature in excess of a safe threshold temperature, and can take appropriate action, such as by disabling the charging coil 44; disabling the generation of therapeutic stimulation pulses; disconnecting the battery 36 from the remainder of the IPG's circuitry, etc.

The inventors consider temperature sensing via thermistor 80 to have certain shortcomings. An IPG 10 may need to understand its temperature to an accuracy of +/−1 C, and over a relatively wide range of temperatures as discussed above. However, off-the-shelf discrete thermistors 80 may not be able to meet this desired level of accuracy. As such, it is typically necessary to calibrate the temperature reported by the thermistor 80. This adds complexity and time to the manufacturing process, and requires additional equipment. For example, the IPGs (preferably at an interim stage in which their circuitries are complete, but their batteries not yet attached) must "soak" at a known temperature (in an oven for example); the temperature of the thermistor 80 is then read by the microcontroller 60; with the microcontroller 60 then making an adjustment to align the reported temperature from the thermistor 80 with the known temperature. This adjustment to compensate for the thermistor 80's lack of accuracy can be internal to the microcontroller 60 (e.g., by altering its programming to converting the reported temperature to an accurate temperature), or by trimming the value of resistor R0. This calibration procedure preferably occurs at more than one temperature (e.g., at or near 0 C and 60 C, and perhaps at intermediate temperatures as well) to ensure proper calibration of the thermistor 80 over its intended operating range. Adding further difficulty to this procedure is that certain circuitry used in connection with reading the thermistor's temperature, such as the Analog-to-Digital Converter 61, may not function well as extreme temperatures, and may produce errors or add to the inaccuracy of the temperature measurement.

Additionally, the thermistor 80 is generally mounted to the IPG's PCB 40, which the inventors do not prefer. Although small, the thermistor 80 needs to be accommodated by the PCB 40, leaving less room for other components, and prohibiting reduction of PCB and IPG size. A surface-mounted thermistor 80 is also susceptible to mechanical damage.

Finally, typical surface-mounted thermistors 80 generally have resistances of 10 k-ohms or lower. The resistive network in which the thermistor 80 is included, which may include resistors of comparable resistance (e.g., R0), may therefore draw currents of at least tens of microAmps at typical levels for the analog-circuitry power supply voltage Va. This is a relatively significant current draw from power supply Va, and thus ultimately from the battery 36. This makes continuous temperature monitoring difficult, as temperature sensing will more quickly deplete a permanent battery 36, or require more frequent charging of a rechargeable battery 36.

BRIEF DESCRIPTION OF THE DRAWINGS

FIGS. 1A and 1B show an implantable pulse generator (IPG) in plan and cross sectional views, in accordance with the prior art.

FIG. 4C shows the signals produced by the circuitries of FIGS. 4A and 4B as a function of temperature, in accordance with an embodiment of the invention.

FIGS. 6A and 6B show different examples of digital circuitry receiving the digital signal(s) from the improved temperature sensing circuitry, in accordance with an embodiment of the invention.

FIGS. 8A-8C show modification to the improved temperature sensing circuitry in which IPG temperature is assessed with respect to only a single temperature threshold, in accordance with an embodiment of the invention.

FIGS. 9A-9C show modification to the improved temperature sensing circuitry in which IPG temperature is assessed with respect to more than two temperature thresholds, in accordance with an embodiment of the invention.

DETAILED DESCRIPTION

Improved temperature sensing circuitry for an Implantable Medical Device (IMD) such as an Implantable Pulse Generator (IPG) is included, although the circuitry can be used in other devices and integrated circuits as well. The circuitry can be included in other integrated circuitry in the IMD, such as Application Specific Integrated Circuits (ASICs) that produce the therapeutic stimulation pulses in the IMD. Temperature sensor and threshold setting circuitry produces analog voltage signals indicative of a sensed temperature and at least one temperature threshold, and preferably both upper and lower temperature thresholds. Such circuitry employs a Ptat current reference stage and additional stages, which stages contains resistances that are set based on the desired temperature threshold(s). These analog voltages are received at temperature threshold detection circuitry, which produces digital signal(s) indicating whether the sensed temperature has passed the temperature threshold(s), and preferably whether the sensed temperature has exceeded the upper temperature threshold or has fallen below the lower temperature threshold. The digital signal(s) are then provided to digital circuitry in the IMD, where they can be stored as a function of time for later review, or used to immediately to control IMD operation. The improved temperature sensing circuitry draws very little power (e.g., 500 nA) compared to thermistor-based approaches used in the prior art, thus enabling continuous temperature monitoring of the IPG without undue depletion of the IPG's battery.

Figure 3:
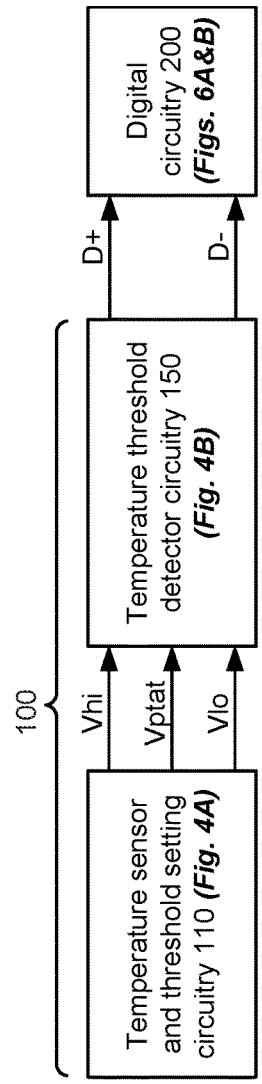
FIG. 3 shows a block diagram of improved temperature sensing circuitry for an IPG, including temperature sensor and threshold setting circuitry and temperature threshold detection circuitry, in accordance with an embodiment of the invention.

The improved temperature sensing circuitry 100 is shown first in FIG. 3, and includes temperature sensor and threshold setting circuitry 110 and temperature threshold detector circuitry 150. Circuitry 110 produces analog signals including Vptat, which indicates the sensed temperature of the IPG, and one or both of Vhi and Vlo, which are set in accordance with desired upper and lower temperature thresholds (Thi and Tlo) as discussed further below. Vptat and one or more of Vhi and Vlo are provided to circuitry 150, which produces one or both digital signals D+ and D−, which respectively indicate to digital circuitry 200 whether the temperature has exceeded Thi (when D+='1') and/or whether the temperature has fallen below Tlo (when D−='1'). Digital circuitry 200 may then take action on the digital signals D+ and/or D−, as explained later.

Figure 4A:
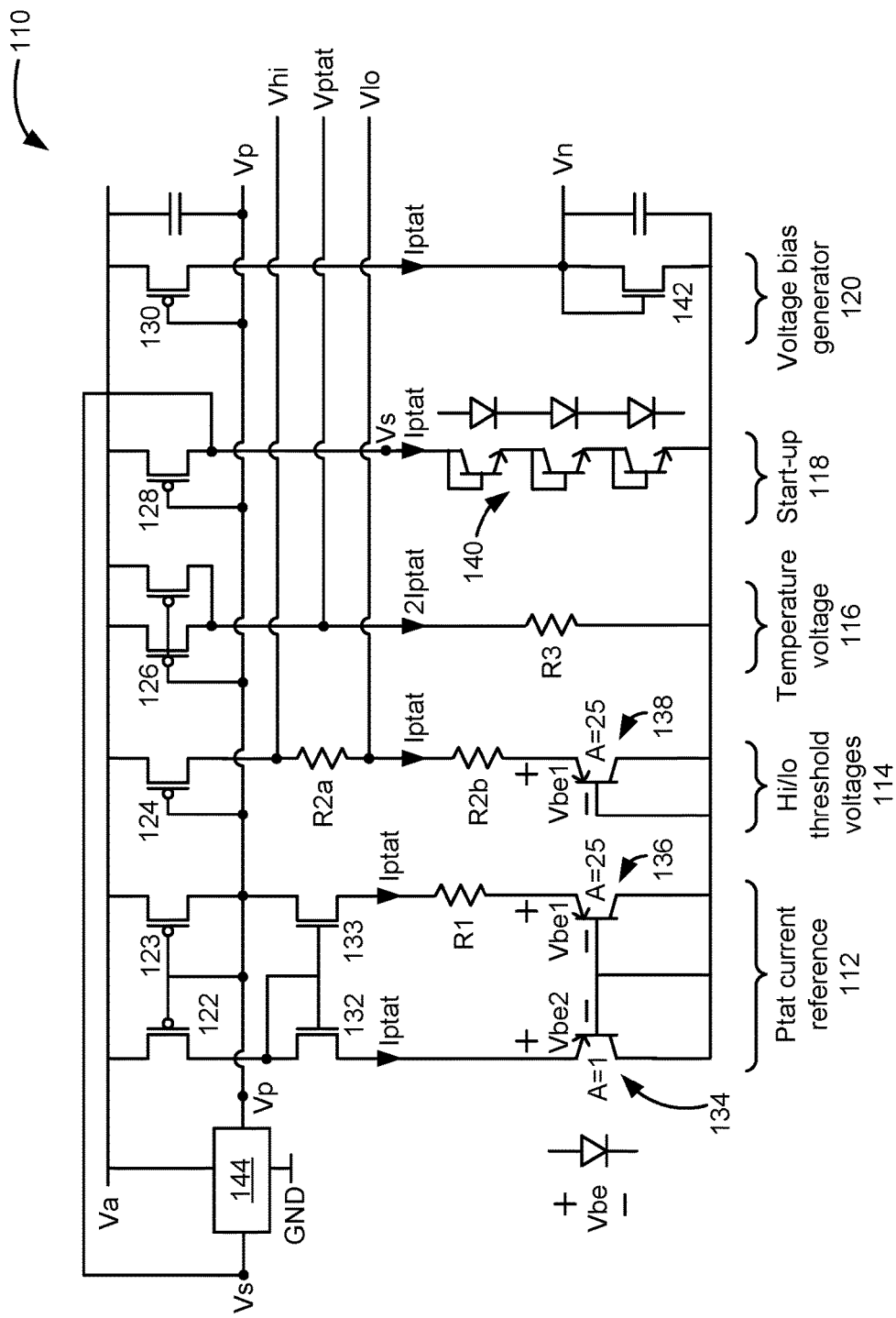
FIG. 4A shows an example of the temperature sensor and threshold setting circuitry, including the generation of analog signals Vptat, Vhi, and Vlo that are used to sense IPG temperature and determine when temperature thresholds have been passed, in accordance with an embodiment of the invention.
Figure 4B:
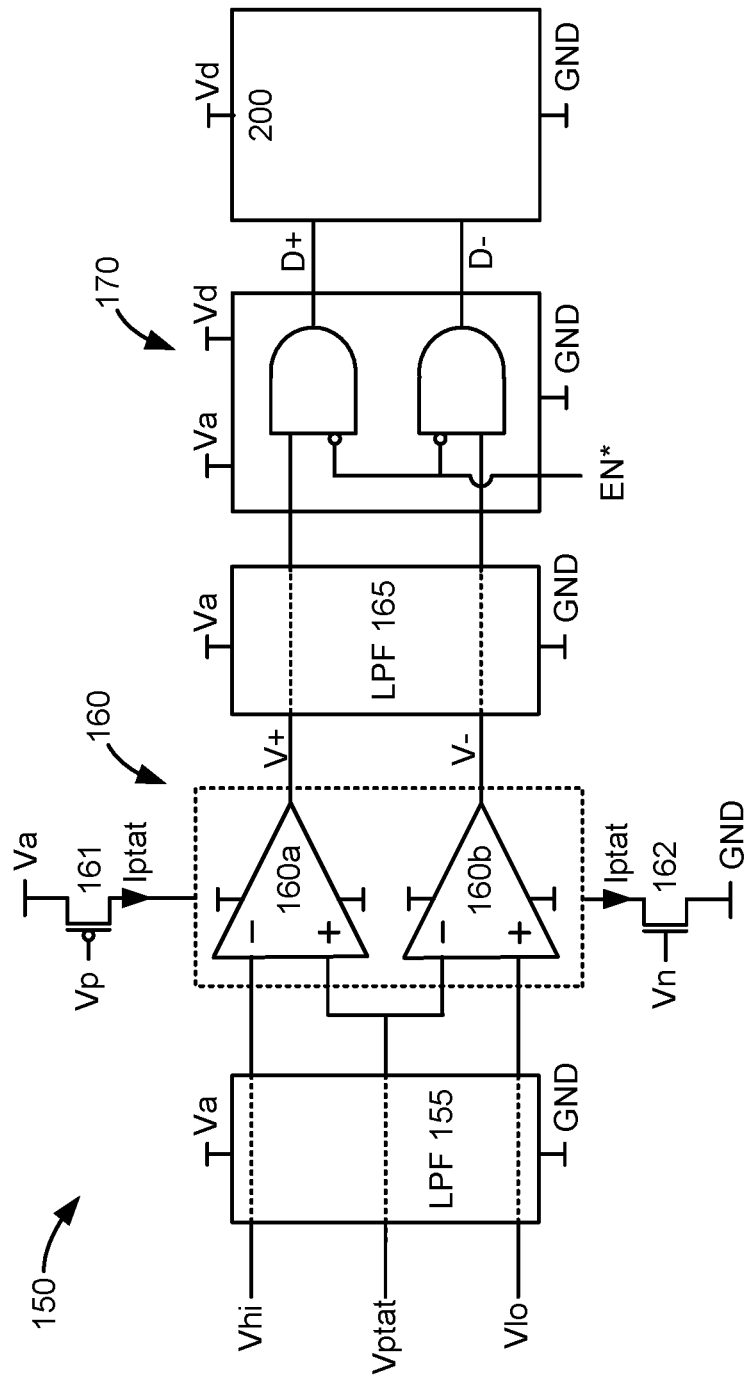
FIG. 4B shows an example of the temperature threshold detection circuitry for interpreting the analog signals and for generating digital signals D+ and D− indicative of the passing of temperature thresholds, in accordance with an embodiment of the invention.

In FIGS. 4A-4C, it is assumed that circuitries 110 and 150 are concerned with assessing IPG temperature relative to upper and lower temperature thresholds Thi and Tlo that define a temperature window appropriate for the IPG. However, this is not strictly necessary, as both circuits can be modified to assess temperature relative to a single temperature threshold, as discussed later with respect to FIGS. 8A-8C, or to assess temperature relative to more than two temperature thresholds, as discussed later with respect to FIGS. 9A-10B. Tlo and Thi are assumed to be 0 C and 60 C in subsequent discussions, although this is not strictly necessary, and other temperature thresholds can be set in circuitry 110, as one skilled in the art will appreciate upon review of this disclosure.

FIG. 4A shows the temperature sensor and threshold setting circuitry 110, which comprises a number of stages 112-120 wired in parallel between the analog-circuitry power supply voltage Va and a reference voltage such as ground.

Stage 112 comprises a well-known Ptat current reference which generates a reference current, Iptat. As shown, the Ptat current reference 112 comprises a cascode current source comprising two current mirrors formed of transistors 122 and 123, and 132 and 133. A matching current Iptat is formed in both of the legs of the Ptat current reference 112. As is known, and thus not explained, Iptat varies positively with temperature (T) as set by the resistance R1 and the ratio A (e.g., 25) of the base-emitter areas of the two PNP transistors 134 and 136, in accordance with the following formula:

$$Iptat = (Vbe2 - Vbe1)/R1 = \Delta Vbe/R1 = kT*\ln(A)/(q*R1) \quad (1)$$

where k=Boltzmann constant ($1.38 \times 10^{-23}$ J/K), and q=electronic charge ($1.60 \times 10^{-19}$ coul). Note that transistors 134 and 136 are wired as diodes, with their collectors and bases shorted. True diodes could be used in their place, and "diode device" is used herein to described both true diode, diode-wired transistors, and like circuitry devices.

R1 is generally selected to restrict Iptat to limit power consumption by the temperature sensor and threshold setting circuitry 110, and may be set at a nominal temperature expected by the IPG 10, preferably within the temperature range of interest. For example, R1 can be set assuming operation of the IPG at 30 C, which is generally close to both room temperature (23 C) and body temperature (37 C) once the IPG 10 is implanted in a patient. 30 C also happens to be the midpoint of the chosen temperature thresholds 0 and 60 C, although setting R1 at this midpoint is not strictly necessary. Assume at 30 C that Iptat is desirably 50 nA for low power draw. If so, R1 can be set by rearranging Equation (1), and by adjusting T=30 C to a Kelvin scale:

$$R1 = k*(30+273.15)*\ln(25)/(q*50n) = 1.7 \, M\text{-ohms} \quad (2)$$

Iptat is mirrored from transistor 123 to transistor(s) 126 to create a representation of Iptat in temperature voltage stage 116. Stage 116 includes a resistor R3, and the voltage drop across this resistor, Vptat, varies positively with temperature and is used in circuitry 110 to indicate the sensed temperature of the IPG:

$$Vptat = 2 Iptat * R3 \quad (3)$$

As Vptat is used to indicate sensed temperature, it may be referred to as a temperature voltage.

Because two current mirror transistors 126 are provided, note that 2 Iptat is passed through stage 116. (A single transistor 126 of twice the width of transistor 123 could also be used). Using a higher current in this stage is preferred to increase the range of variation of Vptat at different temperatures. However, this is not strictly necessary, and other scalars of Iptat could also be used, such as Iptat (as provided by a single transistor 126), or 3 Iptat (as provided by three transistors 126), etc., to vary Vptat over a wider range if necessary.

Iptat is also mirrored from transistor 123 to transistor 124 to create a representation of Iptat in hi/lo threshold voltages stage 114, which forms two voltages Vhi and Vlo set in accordance with the upper and lower temperature thresholds Thi and Tlo, as explained further below. Iptat is received by two resistors R2a and R2b, as well as a diode device 138, and thus:

$$Vhi=Iptat*(R2a+R2b)+Vbe1 \qquad (4)$$

$$Vlo=Iptat*R2b+Vbe1 \qquad (5)$$

As Vhi and Vlo are set in accordance with desired temperature thresholds, as discussed further below, they can be referred to as threshold voltages. Furthermore, as resistors R2a and R2b in stage 114 are used to set the threshold voltages Vhi and Vlo, they can be referred to as threshold resistances.

Note that the voltage drop across diode device 138, Vbe1, varies negatively with temperature, as is well known. Vbe1 is nominally equal to 0.65 V (at 25 C), but changes with temperature at a rate of about −2.0 mV/C. Thus, Vbe1 is about 0.7V at Tlo=0 C, and 0.58V at Thi=60 C.

Start-up stage 118 is optional in temperature sensor and threshold setting circuitry 110, but is useful to ensure that the circuitry 110 will work properly to establish Iptat per Equation (1) when initialized. This occurs passively without receipt of control signals. Iptat is mirrored into start-up stage 118 using transistors 123 and 128. If Iptat is low, as it would be upon initialization, voltage Vs across diode devices 140 will be relatively low. This voltage Vs is sensed and compared to a threshold (e.g., Vs<Vt=1.75V) in a detector 144, which decreases bias voltage Vp provided to the gates of the P-channel current mirror transistors 122-130. Decreasing Vp turns these current mirror transistors 122-130 on more strongly, thus increasing Iptat and increasing Vs. As Iptat rises, it is eventually limited by Equation (1). When Iptat reaches the value prescribed by Equation (1), Vs will be above the threshold in the detector 118 (e.g., Vs>Vt=1.75 V), at which point the detector 118 stops controlling Vp by tri-stating (disconnecting) its output.

Voltage bias generator stage 120 is also optional in temperature sensor and threshold setting circuitry 110, but provides bias voltages Vp and Vn useful in downstream processing of Vptat, Vhi, and Vlo in the temperature threshold detector circuitry 150, as explained later with reference to FIG. 4B. Iptat is mirrored into voltage bias generator stage 120 using transistors 123 and 130, which current also passes through N-channel transistor 142 to generate Vn.

Note that temperature sensor and threshold setting circuitry 110 uses very little power—for example, less than 500 nA—as dictated primarily by the sum of the currents drawn by the various stages 112-120. This is small compared to the capacity of the battery 36, whether rechargeable or not, and much smaller than the current draw required by the thermistor 80 of the prior art as discussed earlier. Accordingly, circuitry 110 enables continuous temperature monitoring of the IPG 10 without undue depletion of the battery 36.

Vhi and Vlo can be set in accordance with desired upper and lower temperature thresholds Thi and Tlo by choosing appropriate values for the resistances R2a and R2b (Equations (3) and (4)) in light of Vptat/R3 (Equation (5)). (Resistor R1 in the Ptat current reference 112 was already chosen (1.7 M-ohms) to generally set Iptat to a desired value (50 nA) via Equations (1) and (2)).

Setting of resistances R2a, R2b, and R3 begins by considering the value of Iptat at the desired temperature thresholds, which can be calculated using Equation (1) above. Per this equation, and using R1 as already set, Iptat=45 nA at Tlo=0 C, and Iptat=55 nA at Thi=60 C.

Once these values for Iptat are established, resistor R3 can be chosen to produce values for Vptat over a range that is appropriate for the analog-circuitry power supply Va, and the temperature threshold detector circuitry 150 (FIG. 4B). For example, it is reasonable to set Vptat=1.1V at Thi=60 C, as this voltage is below Va and of a value that circuitry 150 can process. R3 can then be calculated using Equation (3) above:

$$1.1=2*55n*R3(@T=60) \qquad (6)$$

Solving this equations yields R3=10 M-ohms. With R3 so set, note that Vptat at Tlo=0 C equals 2*45 n*10M=0.9 V per Equation (3), a voltage which is also reasonably handled by the circuitry, but which is significantly different from its value at Thi, thus establishing a significant range for Vptat over the temperature window of interest.

Resistors R2a and R2b in stage 114, which are used to generate Vhi and Vlo, can be chosen in different manners. In a first example, R2a and R2b are chosen to generate Vhi at a constant voltage over the temperature range of interest. Vptat, which increases with temperature, must cross Vhi at Thi=60 C, and so Vhi=Vptat=1.1 V, using the high value for Vptat established earlier. Keeping Vhi constant means Vhi must also equal 1.1 V at Tlo=0 C. From these requirements, the value of the sum of R2a and R2b can be determined using Equation (4) above:

$$1.1=55n*(R2a+R2b)+0.58(@T=60) \qquad (7a)$$

$$1.1=45n*(R2a+R2b)+0.7(@T=0) \qquad (7b)$$

Solving these equations yields R2a+R2b=12 M-ohms. At this value, the voltage drop across R2a and R2b increases with temperature (2 mV/C) at the same rate that Vbe1 decreases with temperature (−2 mV/C), and thus their sum, as reflected in Vhi (Equation 4), remains constant at 1.1 V.

With this sum so set, Vlo can now be considered to allow the individual values of R2a and R2b to be determined. Vptat must cross Vlo at Tlo=0 C, and so Vlo=Vptat=0.9, using the low value for Vptat established earlier. From this requirement, the value of R2b can be determined using Equation (5) above:

$$0.9=45n*R2b+0.7(@T=0) \qquad (8)$$

Solving this equation yields R2b=4.4 M-ohms, and so R2a=12 M−4.4 M=7.6 M-ohms.

In a second example, temperature sensor and threshold setting circuitry 110 can generate Vhi and Vlo as voltages that vary over the temperature range of interest, which amounts to allowing resistor R2a to vary from the value set in the first example. R2b would again equal 4.4 M-ohms as in the first example, and as set by Equation (8) above. With R2b so set, Vhi can now be considered to allow R2a to be set, but without regard to Vhi's value at Tlo. Vptat must cross Vhi at Thi=60 C. That is, Vptat=Vlo=1.1 V at Thi=60 C. From this requirement, the value of R2a can be determined using Equation (4):

$$1.1=55n*(R2a+4.4\ M)+0.58(\text{at } T=60) \qquad (9)$$

Solving this equation yields R2a=5.1 M-ohms.

Other modifications can be made to similarly set Vlo to a constant value over the temperature range of interest. In a third example, R1=1.7 M-ohms, R2a=18 M-ohms, R2b=12 M-ohms, and R3=20 M-ohms, yielding a constant value for Vlo=1.8V throughout the temperature range of interest. The derivation of these resistor values is not shown, but should be clear based on the foregoing description.

With the values of the resistances R1, R2a, R2b, and R3 so established, the resulting signals Vptat, Vhi, and Vlo are illustrated in FIG. 4C for these examples as a function of temperature, with Vptat passing Vhi at Thi and Vlo at Tlo as desired. In summary, fixing R1, R2a, R2b, and R3 appropriately limits the current draw of circuitry 110, and sets the values of temperature thresholds Thi and Tlo as desired for the application at hand.

Whether these thresholds are exceeded is determined by temperature threshold detector circuitry 150, which is shown in detail in FIG. 4B. Circuitry 150 operates to issue upper temperature and lower temperature digital signals D+ and D− which are respectively set when the detected temperature of the IPG passes the Thi and Tlo. Thus, if Vptat>Vhi, the temperature of the IPG is higher than Thi=60 C, and thus D+ is set by circuitry 150 to '1'. If Vptat<Vlo, the temperature of the IPG is lower than Tlo=0 C, and D− is set to '1'. Thus, the IPG is within the temperature window when both D+ and D− equal '0'. Of course, this is not strictly necessary, and D+ and D− can be either '1' or '0' as desired. For example, if Vptat>Vhi, D+ can be set '1', and if Vptat>Vlo, D− can be set to '1'.

Although not strictly required, analog signals Vptat, Vhi, and Vlo, can be processed by a low-pass filter 155 to remove transients and smooth their values. These voltages as filtered are presented to a comparator stage 160 comprising a high-voltage comparator 160a and a low-voltage comparator 160b, which output signals V+ and V− that are the precursors to digital signals D+ and D−, but which are still referenced to the analog-circuitry power supply voltage, Va. Notice that bias signals Vp and Vn as generated in the voltage bias generator stage 120 (FIG. 4A) can be provided to transistors 161 and 160. This allows Iptat from transistor 123 to be mirrored to transistor 161, and Iptat from transistor 142 in stage 120 to be mirrored to transistor 162, which transistors 161 and 162 can then be used to source and sink current to and from the comparators 160a and 160b. While convenient, such means of biasing (powering) the comparators is not strictly necessary. Signals V+ and V− can again be low pass filtered 165 if desired, and are presented to an enable circuit 170.

Enable circuitry 170 receives a digital enable signal, EN*(active low), and receives both the analog-circuitry power supply Va and a digital-circuitry power supply voltage Vd to allow signals V+ and V− to be level shifted to the Vd power supply domain used by the digital circuitry 200. Thus, when it is desired to take a temperature measurement, En* is set to '0', and the values of V+ and V− are ANDed with the complement of the enable signal ('1') and referenced to power supply Vd as digital signals D+ and D− receivable by the digital circuit 200. The enable signal EN* may issue periodically (e.g., every ten seconds), or as needed, as discussed further below with reference to FIGS. 6A-6B.

Note that both the temperature sensor and threshold setting circuitry 110 and the temperature threshold detector circuitry 150 of the improved temperature sensing circuitry 100 are made of standard components easily integrated within an integrated circuit. The temperature sensing circuitry 100 does not rely on the use of the discrete off-chip components such as the thermistor 80 discussed earlier, which saves space on the IPG's PCB 40, and reduces the likelihood of mechanical damage adversely affecting temperature sensing. In a preferred example, circuitry 100 is integrated in the ASIC(s) 65 discussed earlier, although it could also be integrated with the microcontroller 60 or with another integrated circuit in the IPG 10. Circuitry 100 could also comprise its own integrated circuit chip.

The temperature sensor and threshold setting circuitry 110 and the temperature threshold detector circuitry 150 could also be split between different devices. For example, circuitry 110 could be fabricated in the ASIC(s) 65 and circuitry 150 fabricated in the microcontroller 150, in which case analog signals Vptat, Vhi, and Vlo could be routed from the ASIC(s) 65 to the microcontroller 60 by off-bus signals.

Note also that the temperature sensing circuitry 100 is not dependent on the accuracy of the thermistor 80, and doesn't require calibration, thus simplifying IPG manufacture. In this regard, note that the voltages Vptat, Vhi, and Vlo are dependent on Iptat, the resistances R1, R2a, R2b, and R3, and Vbe1 (Equations (3)-(5)). The physics behind Vbe1 are essentially independent of the process used to form the diode devices 134-138 (FIG. 4A), and thus Vbe1 will not vary with process variations inherent in forming integrated circuits on a semiconductive wafer. Thus, Vbe1 does not appreciably affect the accuracy of Vptat, Vhi, or Vlo.

Iptat though will vary, primarily because the resistances R1, R2a, R2b, and R3 may vary with process variations—for example, from wafer to wafer or even across a wafer upon which the integrated circuits are fabricated. However, the design of temperature sensor and threshold setting circuitry 110 is largely immune to such process variations, because variations in the resistances will be compensated for by variation in the reference current Iptat. These variations largely cancel out in circuit 110 to render voltages Vptat, Vhi, and Vlo at accurate and desired values.

Assume for example that the resistances R1, R2a, R2b, and R3 in a particular integrated circuit fabrication of temperature sensor and threshold setting circuitry 110 are 10% higher than desired (i.e., as determined above), possibly due to processing variations in the material used to form these resistances in the integrated circuit (typically polysilicon). The 10% increase in R1 will reduce Iptat by 10% per Equation (1), which will also reduce Iptat in stages 114 and 116 to which it is mirrored. However, because R2a, R2b and R3 are also increased by 10% in these stages, the voltage drops across them (Iptat*Rx) will remain constant. In short, the temperature sensor and threshold setting circuitry 110 self-compensates, even as the values of the resistors change.

Figure 5:
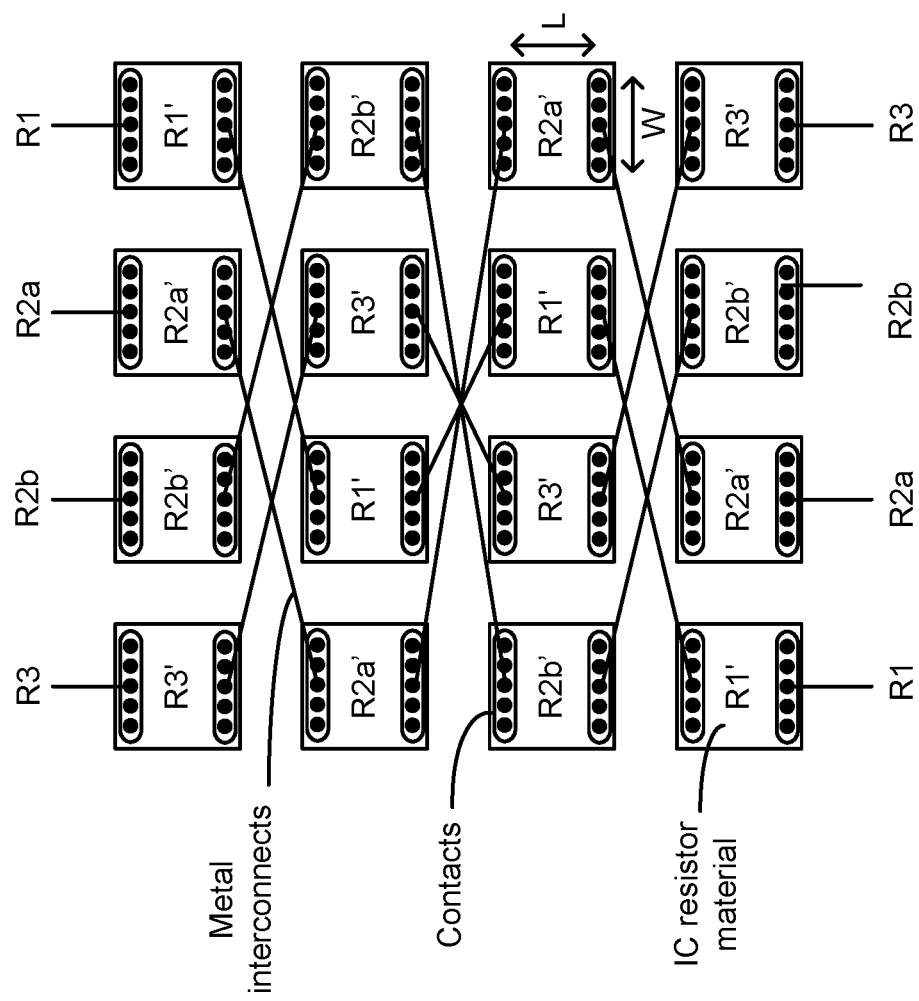
FIG. 5 shows ways in which the resistors in the temperature sensor and threshold setting circuitry can be laid out on an integrated circuit to reduce their variance, in accordance with an embodiment of the invention.

Accuracy can be further promoted by taking measures to assure that the resistances R1, R2a, R2b, and R3 scale equally (i.e., that they all increase or decrease by the same percentage). This may not be a concern as the resistors in each fabricated integrated circuit would generally be laid out in essentially the same location, and processing variations across this location may be insignificant. Nonetheless, the resistors may be laid out on the integrated circuit in this location in manners to reduce their variations with respect to each other. For example, as shown in FIG. 5, the resistors R have been broken into pieces R' (e.g., polysilicon), into quarters in this example, with the pieces R' for each resistor R distributed around the location such that each piece R' in each resistance R will "pick up" processing variations across the location to some degree. The resistor pieces R' are serially connected (using typical integrated circuit metal interconnects and contacts for example) to form each resistance R, which resistances are then connected to other components in circuitry 110 as shown in FIG. 4A.

Because each of the resistances R1, R2a, R2b, and R3 may have different values as discussed above, each piece R' can be sized appropriately to affect the desired resistance. In this regard, each piece R' has a length L and width W, either of which may be adjusted in size to affect its resistance, as is known. Such sizing of the pieces R' for an actual implementation of temperature sensing circuitry 100, i.e., for determined values for R1, R2a, R2b, and R3, is not shown in FIG. 5 for simplicity.

As a result of the self-compensating nature of the temperature sensor and threshold setting circuitry 110, and as potentially further assisted by the resistor layout scheme of FIG. 5, it is estimated that the temperature sensing circuitry 100 can detect temperatures to within +/−1 C over temperature ranges of interest, which accuracy is sufficient for the IPG applications discussed herein without the need for calibration. While calibration of temperature sensing circuitry 100 is not believed necessary, it can still be accomplished, for example, by making one or more of the resistances in circuitry 110 trimmable using fuses or other programming techniques.

Figure 2:
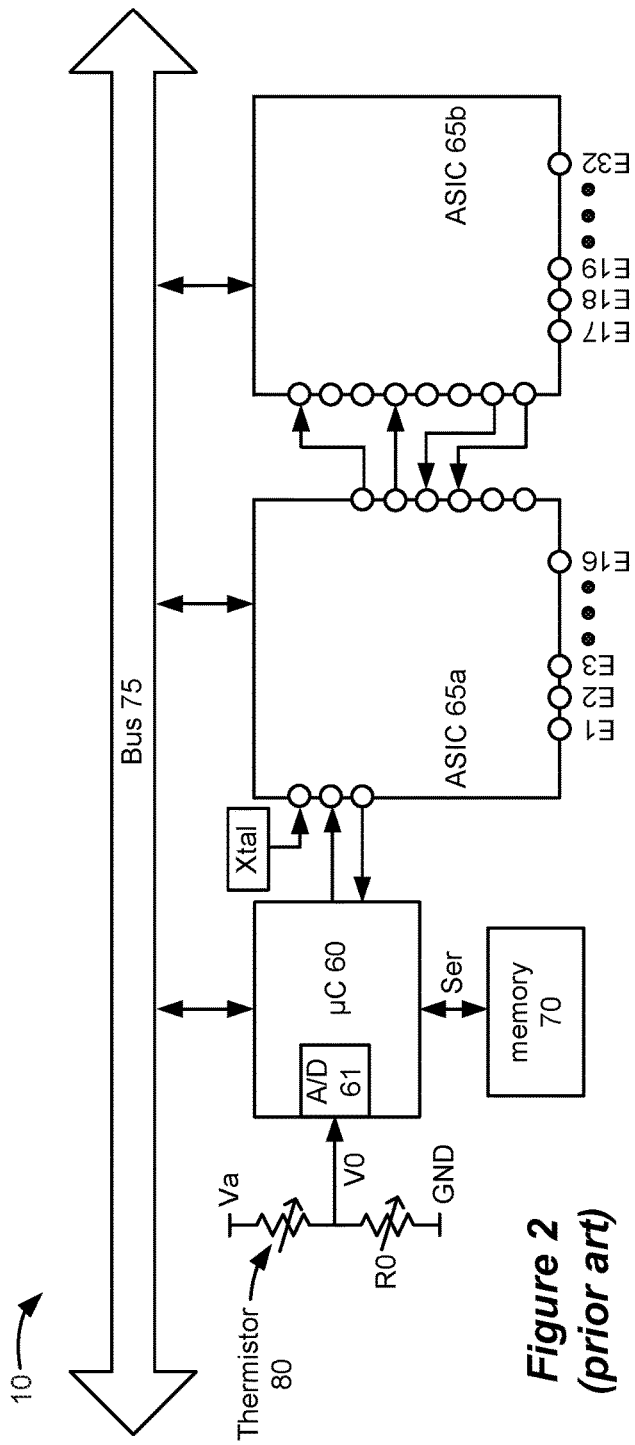
FIG. 2 shows an architecture of the circuitry in the IPG, including the use of an off-chip thermistor to sense IPG temperature, in accordance with the prior art.

FIGS. 6A and 6B show different examples of the digital circuitry 200 which receives the digital signals D+ and D− indicative of IPG temperature, and shows different ways in which the digital circuitry 200 can use this temperature data. Enable signal EN* can be issued by the ASIC(s) 65 or the microcontroller 60 for example, and can be periodically issued to continuously measured IPG temperature, or issued only on command or during prescribed operational modes of the IPG when temperature sensing is desired—in a storage or distribution mode, when providing therapeutic stimulation pulses, when receiving a magnetic charging field, etc. Digital circuitry 200 can comprises circuitry on the ASIC(s) 65 or on the microcontroller 60, or elsewhere in the IPG 10. Note that if temperature sensing circuitry 100 and digital circuitry 200 are on different devices (e.g., with circuitry 100 on the ASIC(s) 65, and digital circuitry 200 on the microcontroller 60), values for D+ and D− can be transmitted to the digital circuitry 200 via the digital bus 75 (FIG. 2) or by off-bus signals.

In FIG. 6A, the digital circuitry 200 comprises a latch or register 202, which continuously updates with the latest values of D+ and D− as the enable signal EN* is asserted. An IPG temperature control circuit 204 continuously monitors the values of D+ and D− in the latch or register 202, and if either signal indicates that a temperature threshold has been passed ('1'), circuit 204 can take immediate action. Many different actions can be taken by circuitry 204, and which actions are taken can depend on whether D+ has been asserted (indicating that the IPG is too hot), or whether D− has been asserted (indicating that the IPG is too cold). Just a few examples of actions the temperature control circuit 204 can take are shown in FIG. 6A, which comprise actions taken to attempt to adjust the temperature of the IPG 10 back within safe limits, or to disable IPG operations that may be unsafe or unreliable if temperature thresholds are surpassed.

For example, circuitry 204 can adjust one or more of the power supplies in the IPG 10, such as the digital-circuitry power supply Vd, or can adjust the speed of the clock used by the IPG. This is particularly useful if the temperature of the IPG is too high (D+='1', as shown), because decreasing Vd and/or the clock speed will tend to reduce the heat generated by the IPG 10. (Alternatively, these parameters could be increased if D− is asserted).

Circuitry 204 may also enable or disable IPG therapy, such as the generation of therapeutic stimulation pulses, when either temperature threshold has passed. This may be done as a safety measure, to protect the patient if the IPG temperature is not within the window defined by Tlo and Thi deemed safe for operation.

Figure 7:
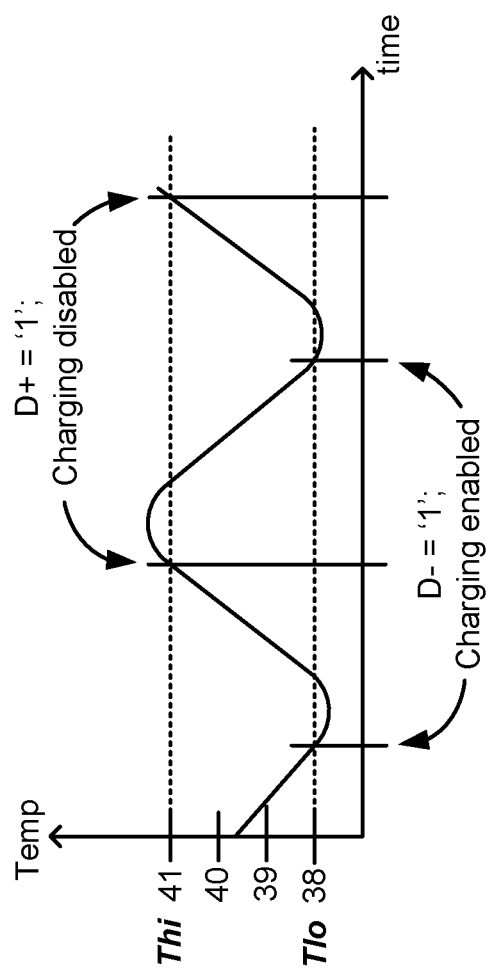
FIG. 7 shows use of the digital circuitry of FIG. 6A to control magnetic inductive charging of an IPG, in accordance with an embodiment of the invention.

Circuitry 204 may also disable or enable charging, as shown more particularly in FIG. 7. As noted earlier, external charging by magnetic induction can heat the IPG 10, and if a safe limit is exceeded (e.g., 41 C), the patient can be injured. Accordingly, an upper temperature threshold of Thi=41 C can be set in the temperature sensor and threshold setting circuitry 110 by appropriate adjustment of the resistor values, as discussed above. A lower temperature threshold of Tlo can also be set (e.g., Tlo=38 C). IPG temperature control circuitry 204 can then monitor D+ and D− in the latch or register 202 in accordance with these thresholds to decide when to enable and disable charging.

As shown in FIG. 7, when D+='1', indicating that Thi=41 C has been surpassed, the IPG 10 can take action by disabling the charging coil 44, for example by grounding or open-circuiting it. Alternatively, the IPG can telemeter passing of this threshold to the external charging device using its telemetry circuitry (on ASIC(s) 65) so that the external charging device may suspend or adjust the magnetic charging field accordingly, for example, as in the '307 Publication cited earlier. Such telemetry can occur for example by Frequency Shift Keying (FSK) as enabled by telemetry coil 42 (FIG. 1B) or by Load Shift Keying (LSK) as enabled by the charging coil 44 as it receives the magnetic field, again as explained in the '307 Publication. When the IPG's temperature has dropped sufficiently, i.e., when D−='1', indicating that Tlo has been surpassed and thus that the IPG 10 has cooled, charging may again be enabled. Alternatively, enabling or disabling charging may occur in accordance with only a single temperature threshold, Tth, with charging disabled when Tth='1' and enabled when Tth='0'. A single temperature threshold embodiment of the improved temperature sensing circuitry 100 is discussed later with respect to FIGS. 8A-8C.

IPG temperature control circuitry 204 can comprise discrete circuitry components such as transistors, resistors, and capacitors, whether integrated in integrated circuitry or not, or can additionally comprise a program operable in the digital circuit 200 (e.g., in microcode).

FIG. 6B illustrates continuous monitoring and storage of IPG temperature by the digital circuitry 200. In this example, the digital circuitry 200 issues the enable signal EN* preferably periodically and continuously over the life of the IPG 10, or at least during some periods of relevance, such as when the devices are being tested or shipped. The values of D+ and D− are stored as a function of time in a memory 210 of the ASIC(s) 65, the microcontroller 60, or another memory associated with these devices (see, e.g., memory 70 in FIG. 2). From time to time, or upon command such as in response to a wireless command received at the IPG's telemetry circuitry from an external device, an IPG temperature algorithm 212 can run to assess the stored temperature data in memory 210.

To cite just one example, the IPG temperature algorithm 212 can assess whether the IPG has ever been subject to temperatures beyond the Tlo and Thi thresholds, such as during its distribution as described earlier, and generate an indication whether the IPG is fit for implantation. In this regard, the algorithm 212 may consider how long the IPG was at an unsuitable temperature. For example, the algorithm 212 may note that the IPG 10 was too hot from times t4-t5 as shown, but may consider that time period too small to suggest that the IPG is unfit. By contrast, the algorithm 212 may note that the IPG 10 was too cold from times t87-t89, which may be too long and may suggest that the IPG is unfit. Thus, one accepting delivery of the IPGs, or a clinician before she is to implant a particular IPG into a patient, can wirelessly review a fitness determination per algorithm 212 transmitted from the IPG's telemetry circuitry to her external device to decide whether IPG can be implanted, or should be returned to the manufacturer.

To this point, it has been assumed that the temperature sensing circuitry 100 assesses IPG temperature with respect to a temperature window defined by upper (Thi) and lower (Tlo) temperature thresholds. However, the circuitry 100 can also be modified to assess IPG temperature with respect to only one temperature threshold, Tth. In the example shown in FIGS. 8A-8C, temperature threshold Tth is analogous to Thi, and thus a voltage Vth is generated by circuitry 110 (FIG. 8A) analogous to Vhi as described earlier (i.e., Vth=Iptat*R4+Vbe1; compare Equation (4)). However, Tth could be analogous to Tlo as well, with Vth generated similarly to Vlo. Circuitry 150 is simplified (FIG. 8B), as only one comparator 160 is needed to compare Vth to Vptat to generate digital signal Dth indicative whether Tth has been surpassed. FIG. 8C shows the resulting waveforms and Dth.

Temperature sensing circuitry 100 is also modifiable to assess temperatures with respect to more than two temperature thresholds, as shown in FIGS. 9A-9C. In this example, temperature sensor and threshold setting circuitry 110 has been modified to include additional resistors (R5x) in stage 114, with analog voltages Vx associated with temperature thresholds Tx generated in between these resistances:

$$V1 = Iptat * R5d + Vbe1 \quad (10a)$$

$$V2 = Iptat * (R5d + R5c) + Vbe1 \quad (10b)$$

$$V3 = Iptat * (R5d + R5c + R5b) + Vbe1 \quad (10c)$$

$$V4 = Iptat * (R5d + R5c + R5b + R5a) + Vbe1 \quad (10d)$$

Temperature thresholds Tx can be chosen for these voltages Vx; the value of Iptat at those temperature thresholds determined (per Equation 1); the value of Vptat at T1 set equal to Equation 10a to determine R5d, and thus determine V1; the value of Vptat at T2 set equal to Equation 10b to determine R5c, and thus determine V2; the value of Vptat at T3 set equal to Equation 10c to determine R5b, and thus determine V3; and the value of Vptat at T4 set equal to Equation 10d to determine R5a, and thus determine V4, similar to the process explained above. The resulting values for V1-V4 once R5a-R5d are set are shown in FIG. 9C, and as before cross Vptat at the various T1-T4 temperature thresholds, allowing the passing of these thresholds to be determined by temperature threshold detector circuitry 150, as shown in FIG. 9B. In this example, digital signal D1 is asserted ('1') when T1 is passed; digital signal D2 is asserted ('1') when T2 is passed, etc., as shown in FIG. 9C. Thus, stage 114 can provide n Vx voltages by using n resistors, allowing for IPG temperature assessment relative to n temperature thresholds Tx.

Figure 10A:
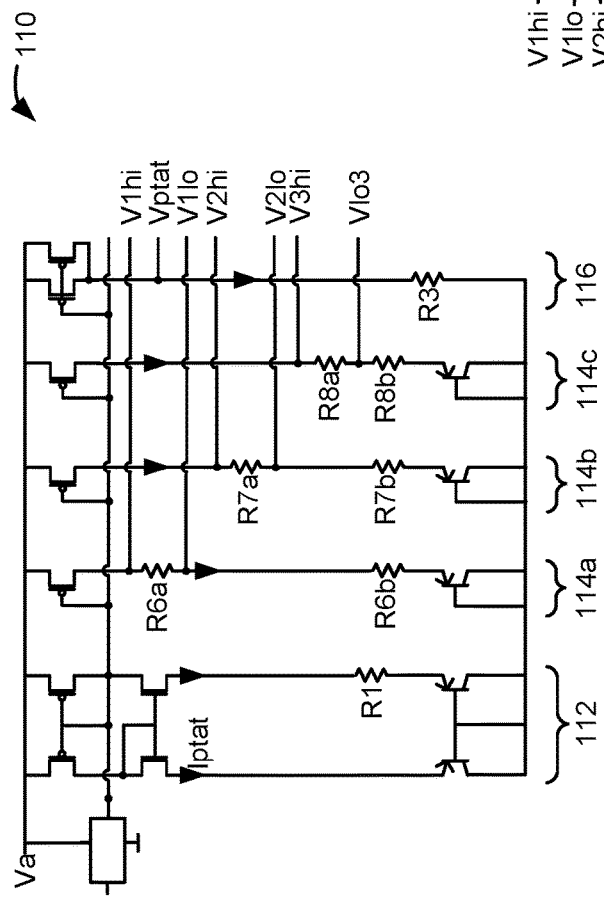
FIGS. 10A and 10B show modification to the improved temperature sensing circuitry in which IPG temperature is assessed with respect to more than two temperature thresholds by adding stages to the temperature sensor and threshold setting circuitry, in accordance with an embodiment of the invention.
Figure 10B:
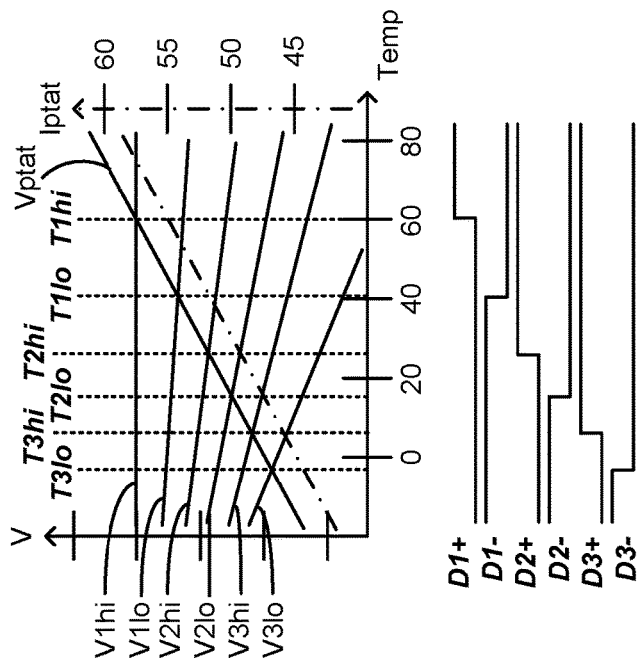

FIGS. 10A and 10B illustrate yet another modification in which extra stages 114 are added to temperature sensor and threshold setting circuitry 110 to provide a multi-threshold temperature sensor. As shown in FIG. 10A, each stage 114 has two resistors Rxa and Rxb, and thus provides a Vxhi and Vxlo signal, similar to that described earlier for FIG. 4A. Lowering the resistance values from stage 114a to 114b to 114c (i.e., R6a>R7a>R8a, and R6b>R7b>R8b) decreases the value of the resulting voltages (V1hi>V2hi>V3hi, and V1lo>V2lo>V3lo), which decreases the temperature thresholds these voltages represent (T1hi>T2hi>T3hi, and T1lo>T2lo>T3lo), as shown in FIG. 10B.

Temperature threshold detector circuitry 150 is not depicted for this modification for simplicity, but it construction should be obvious based on earlier examples, and example digital signals it would produce are shown in FIG. 10B. Digital signals Dx+ and Dx− correspond to the passing by Vptat of Vxhi and Vxlo respectively, in effect defining three different temperature windows as depicted, wherein Dx+ and Dx− both equal '0' when the temperature is between Txhi and Txlo. However, the Dx signals could also be asserted when their associated temperature thresholds are exceeded, as occurs in FIGS. 9B and 9C. Thus, in effect, FIGS. 10A-10C as depicted can be viewed as establishing six temperature thresholds Tx whose passage is indicated by six digital signals Dx, without regard to their being high or low with respect to a two-threshold temperature window.

Stated differently, by providing n stages 114, each with two resistors, temperature sensor and threshold setting circuitry 110 of FIG. 10A can provide 2 n voltages, thus allowing for IPG temperature assessment relative to n temperature thresholds Txhi and n temperature thresholds Txlo, totaling 2 n thresholds Tx. Because each stage 114 can also comprise one (FIG. 8A) or more than two (FIG. 9A) resistors, this conclusion can be further generalized: by providing n stages 114, each with q resistors Rx, temperature sensor and threshold setting circuitry 110 can provide q*n voltages, thus allowing for IPG temperature assessment relative to q*n temperature thresholds Tx. Note that adding additional stages 114, each receiving Iptat via a current mirror, increases the power draw of the temperature sensor and threshold setting circuitry 110.

Figure 11A:
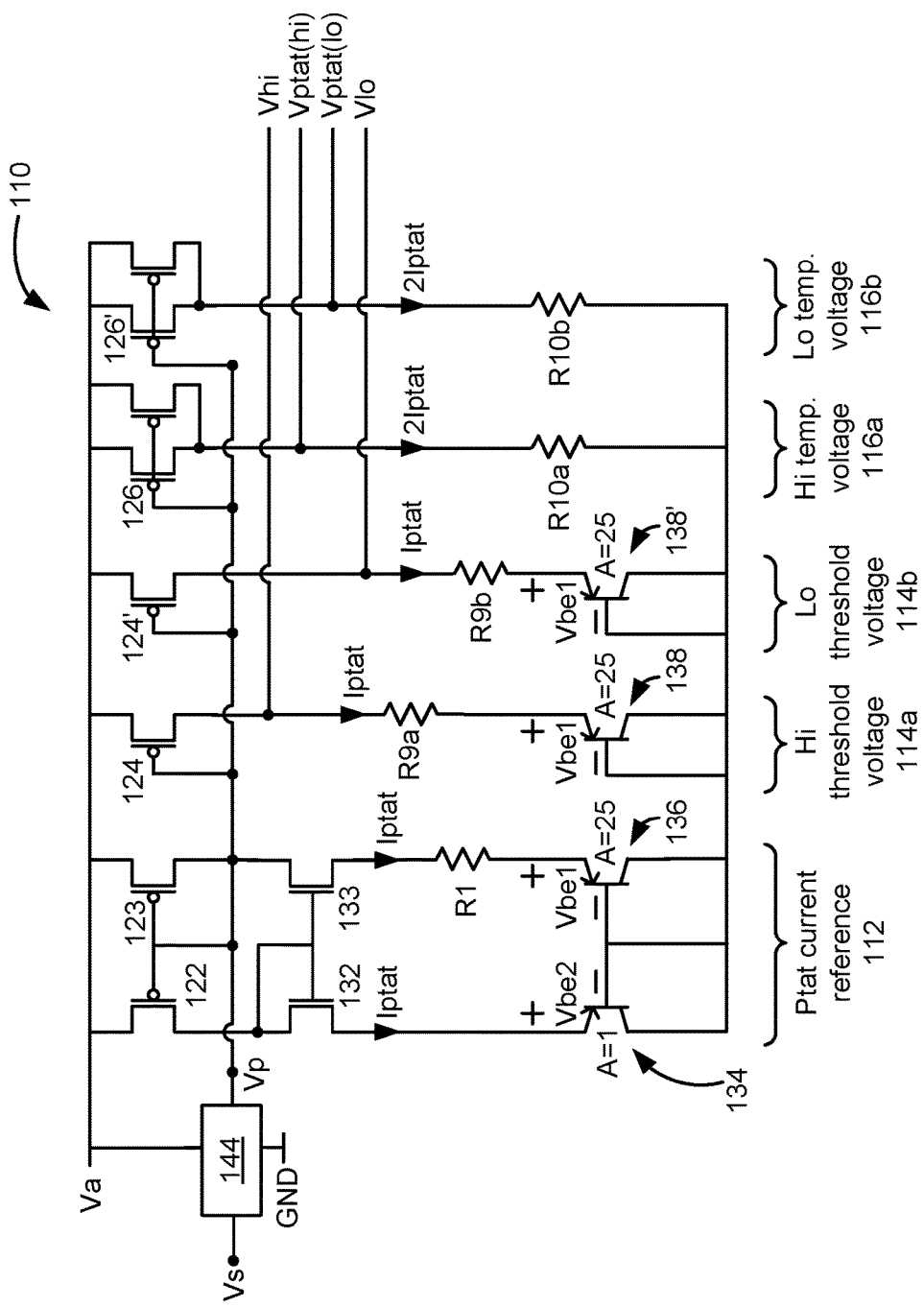
FIGS. 11A-11C show modification to the improved temperature sensing circuitry in which both the Vhi and Vlo signals produced do not vary with temperature, in accordance with an embodiment of the invention.

Additional stages can be used in the temperature sensor and threshold setting circuitry 110 for other purposes. For example, in FIGS. 11A-11C, Vhi and Vlo are generated in separate stages 114a and 114b, and different Vptat voltages Vptat(hi) and Vptat(lo) are generated for each in stages 116a and 116b. This is particularly useful if it is desired to render both Vhi and Vlo as constant over the temperature range of interest, which requires the use of different resistor values in these stages.

For example, R9a in stage 114a and R10a in its associated stage 116a can be set as determined earlier in Example 1 of FIG. 4C, which illustrated the generation of a constant Vhi=1.1V. R9a can be set by adding the determined values for R2a and R2b in that example, and so R9a equals 12 M-ohms. R10a can be set per R3 in that example as 10 M-ohms. As explained earlier, these resistor values will establish Vhi at a constant value of 1.1V, and establishes Vptat(hi) so that it crosses Thi at this value. R9b in stage 114b and R10b in associated stage 116b can be set as determined earlier in Example 3 of FIG. 4C, which illustrated the generation of a constant Vlo=1.8V: R9b can again be set by adding R2a and R2b in that example, and so R9b equals 30 M-ohms. R10b can be set per R3 in that example as 20 M-ohms. As explained earlier, these resistor values will establish Vlo at a constant value of 1.8V, and establishes Vptat(lo) so that it crosses Tlo at this value. This is shown graphically in FIG. 11C, which in large part comprises an overlay of Examples 1 and 3 as depicted in FIG. 4C.

Figure 11B:
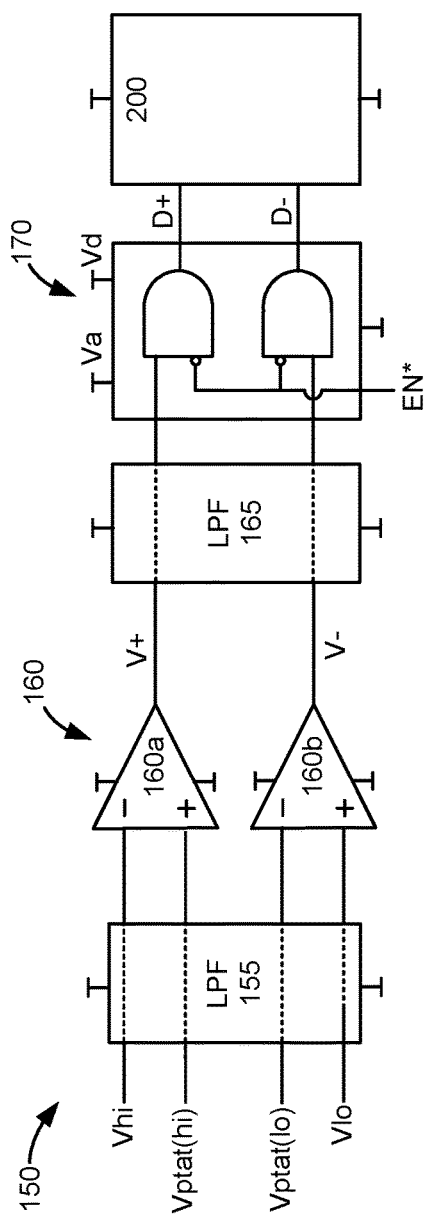
Figure 11C:
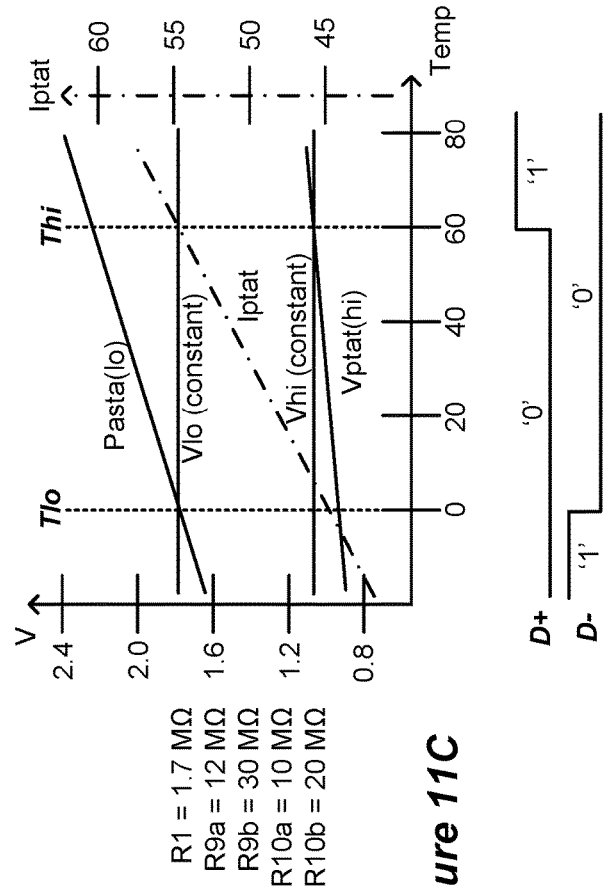

FIG. 11B shows temperature threshold detector circuitry 150 useable with this embodiment, and as shown Vhi is compared to Vptat(hi) in comparator 160a, while Vlo is compared with Vptat(lo) in comparator 160b. This leads to the generation of digital signal D+ and D− as before, with D+ asserted when the temperature is higher than Thi, and D− asserted when the temperature is lower than Tlo, again as shown in FIG. 11C. As noted earlier, the digital signals can toggle in either direction (from '0' to '1', or vice versa) when the temperature increases beyond its associated threshold.

Figure 12:
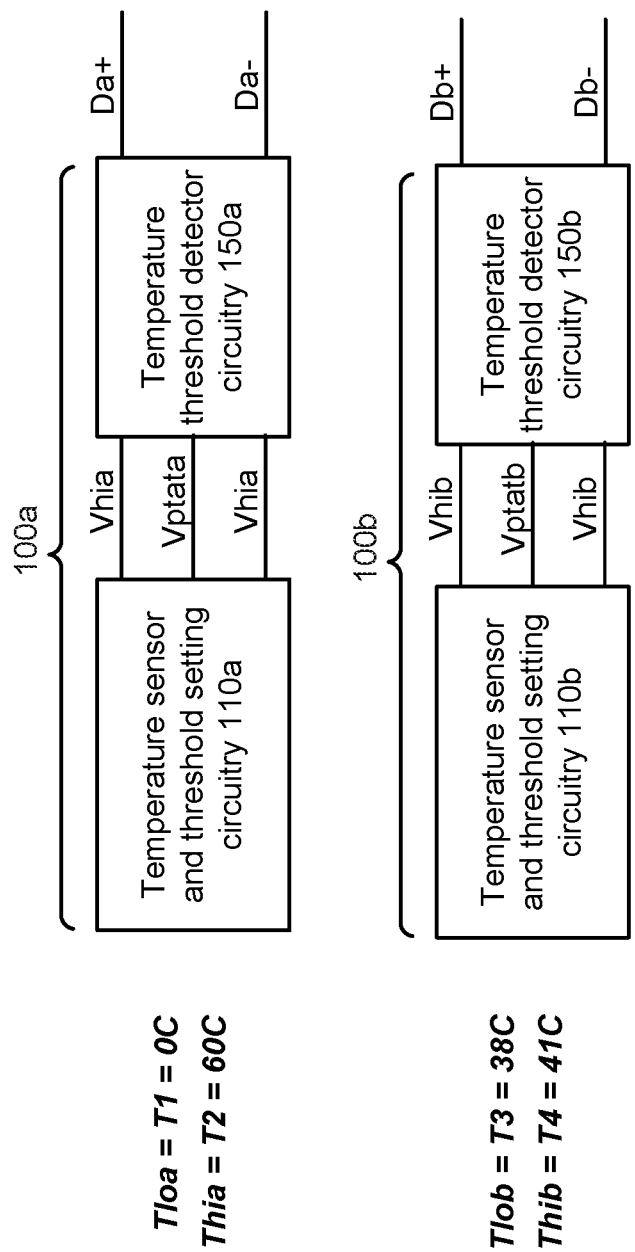
FIG. 12 shows duplication of the improved temperature sensing circuitry used to assess IPG temperature with respect to two temperature windows, in accordance with an embodiment of the invention.

FIG. 12 shows another example in which more than one temperature sensing circuitries 100 are used in the IPG 10. In this example, two circuits 100a and 100b are used, with their resistors set to detect temperatures between Tloa=0 C and Thia=60 C in circuitry 110a, and between Tlob=38 C and Thib=41 C in circuitry 110b. Thus, circuitry 100a detects extreme temperatures with respect to a larger temperature window, as useful to assess IPG temperature during distribution, while circuitry 100b assesses temperatures with respect to a smaller temperature window, as useful during magnetic inductive charging, as described earlier with reference to FIG. 7. Still other temperature sensing circuits 100 could be included to assess IPG temperatures versus a single temperatures threshold, a window defined by two temperature thresholds, or a plurality of temperature thresholds, again in the various ways set forth above.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. Temperature sensing circuitry, comprising:
   temperature sensor and threshold setting circuitry configured to produce a temperature voltage that varies positively with temperature, and two threshold voltages each indicative of a temperature threshold, wherein the two threshold voltages are set by at least one threshold resistance; and
   temperature threshold detector circuitry configured to compare the temperature voltage with each of the two threshold voltages, wherein the temperature threshold detector circuitry is configured to produce from each comparison a digital signal for each threshold voltage, wherein each digital signal indicates whether the temperature voltage has passed a temperature threshold set by one of the two threshold voltages.

2. The circuitry of claim 1, wherein the temperature sensor and threshold setting circuitry produces the temperature voltage and the two threshold voltages passively without receipt of control signals.

3. The circuitry of claim 1, wherein the temperature sensor and threshold setting circuitry comprises a plurality of stages wired in parallel between a power supply voltage and a reference voltage.

4. The circuitry of claim 3, wherein a first of the plurality of stages is configured to produce a reference current dependent on the sensed temperature.

5. The circuitry of claim 4, wherein the first stage comprises a Ptat current reference comprising two diode devices, wherein the reference current is determined by a first resistance in the first stage and a ratio of areas of the two diode devices.

6. The circuitry of claim 4, wherein a second of the plurality of stages produces the two threshold voltages, and wherein a third of the plurality of stages produces the temperature voltage.

7. The circuitry of claim 1, wherein the temperature threshold detector circuitry comprises two comparators, each comparator configured to compare the temperature voltage with one of the two threshold voltages to produce one of the digital signals.

8. The circuitry of claim 1, further comprising a digital circuit configured to receive the digital signals.

9. The circuitry of claim 8, wherein the digital circuit comprises a memory to store values of the digital signals produced at different times.

10. The circuitry of claim 9, wherein the digital circuit is programmed with a temperature algorithm configured to review the values of the digital signals in the memory.

11. The circuitry of claim 10, wherein the circuitry is within an implantable medical device, and wherein the algorithm is configured to review the values of the digital signals to determine whether the implantable medical device is fit for implantation in a patient.

12. The circuitry of claim 11, further comprising telemetry circuitry configured to wirelessly transmit the fitness determination to an external device.

13. The circuitry of claim 8, wherein the digital circuit comprises latches or registers to hold latest values of the digital signals.

14. The circuitry of claim 8, wherein the digital circuit comprises a temperature control circuit configured to review the digital signals, and to take an action if at least one of the digital signals indicates that at least one temperature threshold has been passed.

15. The circuitry of claim 14, further comprising a charging coil for receiving a magnetic charging field from an external device, wherein the action comprise disabling or enabling of the charging coil.

16. The circuitry of claim 14, further comprising telemetry circuitry, wherein the action comprises telemetering from the telemetry circuitry to an external device an indication that at least one temperature threshold has been passed.

17. The circuitry of claim 14, further comprising a power supply voltage or a clock, and wherein the action comprises adjusting the power supply voltage or a speed of the clock.

18. The circuitry of claim 14, wherein the circuitry is within an implantable medical device, and wherein the action comprises disabling or enabling the provision of therapy from the implantable medical device to the patient.

19. The circuitry of claim 1, wherein the temperature threshold detector circuitry further comprises an enable circuit configured to produce the digital signals in accordance with an enable signal.

20. The circuitry of claim 19, wherein the enable signal is issued periodically.

* * * * *